United States Patent
Rhee et al.

(10) Patent No.: US 10,849,941 B2
(45) Date of Patent: Dec. 1, 2020

(54) METHOD FOR PREVENTING OR TREATING COLITIS DISEASE COMPRISING *LACTOBACILLUS SAKEI* K040706 AS AN ACTIVE INGREDIENT

(71) Applicant: KOREA FOOD RESEARCH INSTITUTE, Gyeonggi-do (KR)

(72) Inventors: Young Kyoung Rhee, Seongnam-si (KR); Hee-Do Hong, Seongnam-si (KR); Chang-Won Cho, Seoul (KR); Mi Jang, Suwon-si (KR); Tae-Gyu Lim, Seongnam-si (KR); Young-Chul Lee, Seongnam-si (KR); KyungTack Kim, Seoul (KR); Eun-Young Hwang, Seongnam-si (KR); Kyung-Tae Lee, Seoul (KR); Ji-Sun Shin, Seoul (KR); Seunghwan Seo, Seoul (KR); Young-ran Song, Jeonju-si (KR)

(73) Assignee: KOREA FOOD RESEARCH INSTITUTE, Gyeonggi-Do (KR)

( * ) Notice: Subject to any disclaimer, the term of this patent is extended or adjusted under 35 U.S.C. 154(b) by 0 days.

(21) Appl. No.: 16/380,652

(22) Filed: Apr. 10, 2019

(65) Prior Publication Data
US 2019/0224255 A1 Jul. 25, 2019

Related U.S. Application Data

(63) Continuation-in-part of application No. 15/643,712, filed on Jul. 7, 2017, now abandoned.

(30) Foreign Application Priority Data
Jul. 15, 2016 (KR) .................. 10-2016-0089733

(51) Int. Cl.
| | | |
|---|---|---|
| A61K 35/747 | (2015.01) | |
| A23L 33/135 | (2016.01) | |
| A61P 37/00 | (2006.01) | |
| A61P 1/00 | (2006.01) | |

(52) U.S. Cl.
CPC .......... *A61K 35/747* (2013.01); *A23L 33/135* (2016.08); *A61P 1/00* (2018.01); *A61P 37/00* (2018.01)

(58) Field of Classification Search
CPC ....... A23L 33/135; A61K 35/747; A61P 1/00; A61P 37/00; Y02A 50/475; Y02A 50/483
See application file for complete search history.

(56) References Cited

FOREIGN PATENT DOCUMENTS

| KR | 1020070071911 | 7/2007 |
|---|---|---|
| KR | 1020150088702 | 8/2015 |
| KR | 1020150146461 | 12/2015 |

OTHER PUBLICATIONS

Jung et al. (Int. Immunopharmacol. Available Online Jun. 3, 2015. Sep. 2015; 28(1):88-96). (Year: 2015).*

(Continued)

*Primary Examiner* — Jana A Hines
(74) *Attorney, Agent, or Firm* — Leason Ellis LLP

(57) ABSTRACT

Disclosed is a method for treating a colitis disease in a subject in need thereof, the method comprising administering a composition comprising *Lactobacillus sakei* K040706 (Accession No: KCCM11472P) as an active ingredient to the subject in an amount effective in treating the colitis disease.

3 Claims, 13 Drawing Sheets
(2 of 13 Drawing Sheet(s) Filed in Color)
Specification includes a Sequence Listing.

(56) References Cited

OTHER PUBLICATIONS

Park et al.,(FASEB Journal. Published Apr. 2012) i (Year: 2012).*
Kim et al., (J. of Functional Foods. vol. 11, Nov. 2014, pp. 417-427 (Year: 2014).*
Remington's Pharmaceutical Science, 19th ed., Mack Publishing Company, Easton, Pa., 1995.
Non-Final Office Action in corresponding U.S. Appl. No. 15/643,712, dated Aug. 23, 2018.
Seunghwan Seo, et al., "Anti-Colitic and Anti-Inflammatory Effects of Lactobacillus sakei K040706 in Mice with Ulcerative Colitis," World Academy of Science, Engineering and Technology Internationnal Journal of Biotechnology and Bioengineering, 2016, vol. 3, No. 5, (Abstract), 1 page.

\* cited by examiner

METHOD FOR PREVENTING OR TREATING COLITIS DISEASE COMPRISING *LACTOBACILLUS SAKEI* K040706 AS AN ACTIVE INGREDIENT

CROSS-REFERENCE TO RELATED APPLICATIONS

The present application is a continuation-in-part application of U.S. patent application Ser. No. 15/643,712, filed on Jul. 7, 2017, which claims priority to Korean Patent Application No. 10-2016-0089733, filed on Jul. 15, 2016, which are incorporated by reference in their entireties.

INCORPORATION BY REFERENCE OF SEQUENCE LISTING

A sequence listing created on Sep. 20, 2017 as the ASCII text file "10524_006058_US0_Sequence_Listingv2" having a file size of 1,776 bytes, is incorporated herein by reference in its entirety.

FIELD OF THE INVENTION

The present invention relates to a composition for preventing or treating colitis comprising *Lactobacillus sakei* K040706 as an active ingredient. More particularly, the present invention relates to a pharmaceutical composition or a food composition for preventing or treating colitis comprising *Lactobacillus sakei* K040706 (Accession No: KCCM11472P) as an active ingredient.

BACKGROUND OF THE INVENTION

Colitis is an inflammation of the colon, which is caused by various causes. Its major symptoms include tenesmus (a feeling of incomplete excretion), abdominal bloating, abdominal pain, diarrhea, and occasionally mucus, pus, or blood in the feces. Colitis may be classified into infectious colitis and non-infectious colitis depending on its cause. It may be classified into acute colitis and chronic colitis according to its onset period. Acute colitis includes amoebic dysentery, bacterial dysentery, pseudomembranous enteritis caused by salmonella or antibiotics, and the like. Chronic colitis includes ulcerative colitis, Crohn's disease, tuberculosis, syphilis, colitis by X-rays, and the like. In addition, colitis includes inflammatory bowel disease (IBD) as well as irritable bowel syndrome (IBS), and the like.

The causes of ulcerative colitis (UC) and Crohn's disease (CD), the most common inflammatory bowel disease (IBD), have yet to be clarified, while these diseases can cause severe chronic diarrhea and bloody diarrhea with abdominal pain, and are characterized by difficulty in curing and repeated improvement and deterioration. Ulcerative colitis is a disease in which erosions and ulcers are continuously formed in the mucous membranes of the colon and causes bloody excrement, femafecia, diarrhea and abdominal pain. In severe cases of ulcerative colitis, systemic symptoms such as fever, weight loss and anemia appear. Ulcerative colitis may also occur in any part of the gastrointestinal tract. Crohn's disease is a disease in which lesions such as ulcers are generated discontinuously in any part of the digestive tract from the mouth to the anus. And Crohn's disease is accompanied by abdominal pain, diarrhea, and bloody excrement, and severe symptoms include fever, hemorrhage, weight loss, general malaise, and anemia, and the like. Although ulcerative colitis and Crohn's disease are different in their lesions and inflammatory symptoms, they are similar in many respects, so the distinction between the two diseases is often unclear.

Probiotics, on the other hand, are living microbial agents that have beneficial effects by improving the balance of intestinal microorganisms in animals. Lactic acid bacteria is mainly used as probiotics, and a yeast such as *Saccharomyces cerevisiae*, and a mold such as *Aspergillus oryzae* are used. The effects of probiotics include antibiotic-related diarrhea, intestinal infections caused by pathogenic bacteria, improvement of gastrointestinal diseases such as irritable bowel syndrome, reduction of atopic dermatitis, improvement of hypertension, reduction of blood cholesterol level and improvement of blood lipid status, anti-obesity effect, and anti-cancer effects against colon cancer and stomach cancer, and the like. And various functionalities of probiotics are being studied. Recently, studies on the isolation of lactic acid bacteria having probiotic function in traditional fermented foods such as kimchi, salted fish, and soy sauce have been conducted. Thus, health-functional lactic acid bacteria have been discovered in traditional foods.

The present inventors have filed a patent application for *Lactobacillus sakei* isolating and identifying lactic acid bacteria having excellent acid resistance, salt resistance and antibacterial activity from kimchi and its use (a Laid-open Application Publication No. 10-2007-0071911). In addition, a patent application for a method of culturing *Lactobacillus sakei* having immune enhancement function and multifunctionality of improving sensory and quality of food (a Laid-open Application Publication No. 10-2015-0146461) was filed. However, further studies on the health effects of this strain, *Lactobacillus sakei*, are needed.

SUMMARY OF THE INVENTION

An exemplary embodiment provides a method for treating a colitis disease in a subject in need thereof, the method comprising administering a composition comprising *Lactobacillus sakei* K040706 (Accession No: KCCM11472P) as an active ingredient to the subject in an amount effective in treating the colitis disease, wherein the colitis disease is selected from the group consisting of acute enteritis, bacterial colitis, bacterial dysentery, cholera, typhoid, traveler's diarrhea, viral colitis, pseudomembranous colitis, amoebic colitis, inflammatory bowel disease, Crohn's disease, ulcerative colitis, ischemic colitis, Behcet's colitis, drug-induced colitis, microscopic colitis, collagenous colitis, lymphocytic colitis and radiation colitis.

Another exemplary embodiment provides the above mentioned method wherein the composition comprises a dead cell or culture preparation of *Lactobacillus sakei* K040706.

Further exemplary embodiment provides the above mentioned method wherein the composition is a pharmaceutical composition or a food composition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
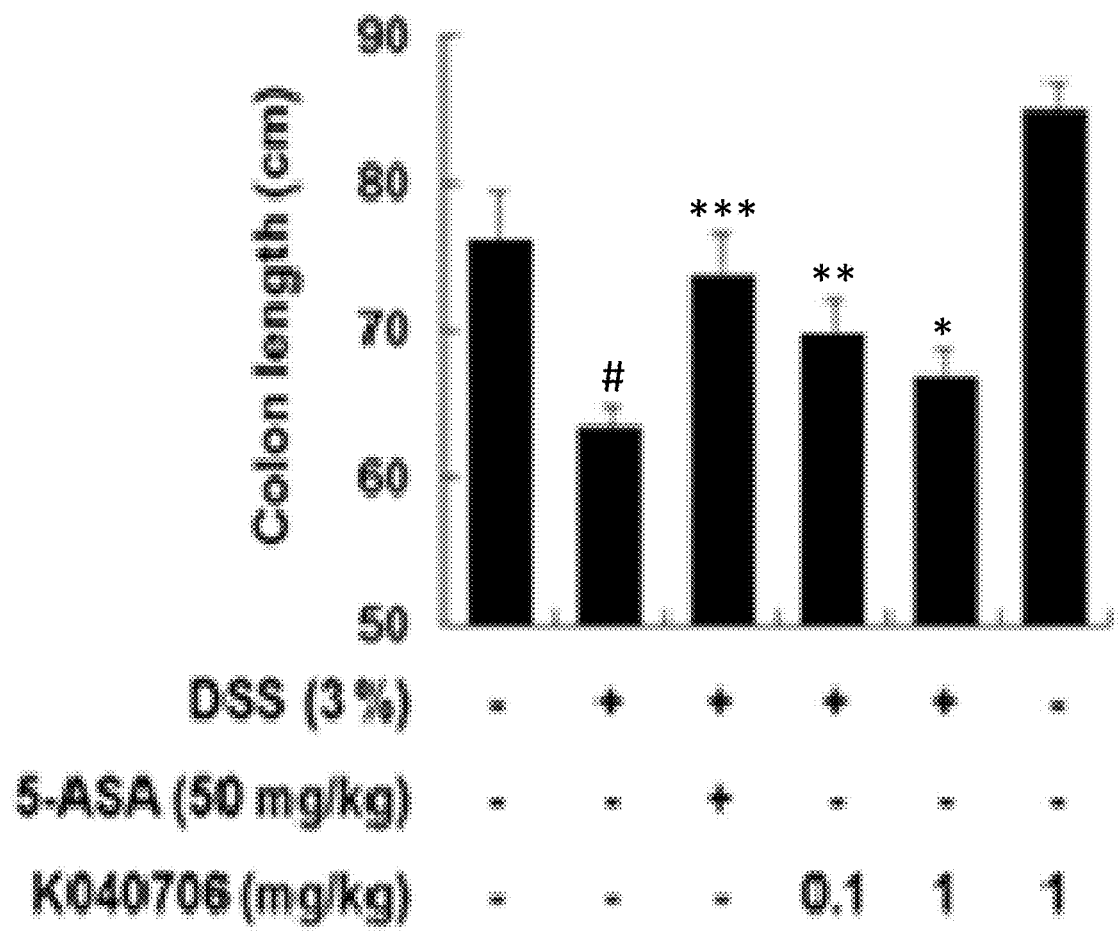
FIGS. 1A-B show the results of measuring the length of the colon (A) and the weight of spleen (B). *Lactobacillus sakei* K040706 dead cells were injected into a colitis mouse model and the measurement was made at day 13.

Hereinafter, the present invention will be described in detail.

The present invention provides a pharmaceutical composition for preventing or treating colitis comprising *Lactobacillus sakei* K040706 (Accession No: KCCM11472P) as an active ingredient.

As used herein, the bacterium of *Lactobacillus sakei* K040706 contains not only the live bacteria itself obtained from the culture medium, but also any processed form of the lactic acid bacteria known to those skilled in the art. But it includes, but is not limited to, for example, cell lysate, dried product, frozen product, culture, fermented product and the like. Also included are a culture medium itself cultured in a liquid medium, and a workpiece derived from the culture medium itself such as a filtrate (centrifuged supernatant) obtained by removing the strain by filtration or centrifugation of the culture medium.

As used herein, it is characterized by being dead cells or culture preparations of *Lactobacillus sakei* K040706.

As used herein, the term "dead cells" refers to bacterial cells that have been sterilized by heating, pressurization, or drug treatment and the like. In addition, a bacterial cell component refers to a product obtained by disrupting a cell or disrupting a cell wall fraction by enzyme treatment, homogenization, ultrasonic treatment or the like. In an example of the present invention, *Lactobacillus sakei* was heated and sterilized at 80° C. for 30 minutes and then dried to obtain a dead cell powder of *Lactobacillus sakei* K040706. The drying method may be freeze drying, spray drying, and drying under reduced pressure, but is not limited thereto.

As used herein, "colitis" is a state in which an inflammation has occurred in the colon due to a variety of causes. It is classified into infectious colitis and non-infectious colitis, depending on its cause. Acute infectious colitis occurs worldwide with its major symptoms of fever, nausea, vomiting, mucus or bloody diarrhea and abdominal pain. IBD (Inflammatory Bowel Disease), which is a noninfectious colitis, is a chronic condition that causes diarrhea, abdominal pain, bloody excrement, weight loss, and recurrence is common. Since a surgery is required if medical treatment is not effective on IBD or complications such as hemorrhage and perforation occur, accurate diagnosis and treatment are important.

Preferably, the kind of colitis is not particularly limited, but is selected from the group consisting of, for example, acute enteritis, bacterial colitis, bacterial dysentery, cholera, typhoid, traveler's diarrhea, viral colitis, pseudomembranous colitis, amebic colitis, inflammatory bowel disease, Crohn's disease, ulcerative colitis, ischemic colitis, Behcet's colitis, drug-induced colitis, microscopic colitis, collagenic colitis, lymphoid colitis, and radiation colitis.

The pharmaceutical composition according to the present invention contains *Lactobacillus sakei* K040706 alone or can be formulated into a suitable form together with a pharmaceutically acceptable carrier, and may further contain an excipient or a diluent. As used herein, the term "pharmaceutically acceptable" refers to a nontoxic composition that is physiologically acceptable and does not usually cause an allergic reaction such as gastrointestinal disorder, dizziness, or the like when administered to humans.

The pharmaceutically acceptable carrier may further include, for example, a carrier for oral administration or a carrier for parenteral administration. Carriers for oral administration may include lactose, starch, cellulose derivatives, magnesium stearate, stearic acid, and the like. In addition, it may contain various drug delivery materials used for oral administration to peptide preparations. In addition, the carrier for parenteral administration may contain water, a suitable oil, a saline solution, an aqueous glucose and a glycol, and may further contain a stabilizer and a preservative. Suitable stabilizers include antioxidants such as sodium hydrogen sulfite, sodium sulfite or ascorbic acid. Suitable preservatives include benzalkonium chloride, methyl- or propyl-paraben and chlorobutanol. The pharmaceutical composition of the present invention may further contain a lubricant, a wetting agent, a sweetener, a flavoring agent, an emulsifying agent, a suspending agent and the like in addition to the above components. Other pharmaceutically acceptable carriers and preparations can be referred to those described in the following references (Remington's Pharmaceutical Sciences, 19th ed., Mack Publishing Company, Easton, Pa., 1995).

The composition of the present invention can be administered to mammals including humans by any method. For example, it can be administered orally or parenterally. Parenteral administration methods include, but are not limited to, intravenous, intramuscular, intraarterial, intramedullary, intrathecal, intracardiac, transdermal, subcutaneous, intraperitoneal, intranasal, enteral, topical, sublingual or rectal administration.

The pharmaceutical composition of the present invention may be formulated into oral or parenteral administration preparations according to the administration route as described above.

In the case of oral administration preparations, the composition of the present invention may be formulated into powder, granules, tablets, pills, sugar tablets, capsules, liquids, gels, syrups, slurries, suspensions or the like using methods known in the art. For example, an oral preparation can be obtained tablets or sugar tablets by combining the active ingredient with a solid excipient, then milling it, adding suitable auxiliaries, and processing the mixture. Examples of suitable excipients include sugars including lactose, dextrose, sucrose, sorbitol, mannitol, xylitol, erythritol and maltitol, and starches including corn starch, wheat starch, rice starch and potato starch, cellulose such as cellulose, methyl cellulose, sodium carboxymethyl cellulose and hydroxypropylmethyl cellulose and the like, fillers such as gelatin, polyvinylpyrrolidone and the like. In addition, crosslinked polyvinylpyrrolidone, agar, alginic acid or sodium alginate may optionally be added as a disintegrant. Further, the pharmaceutical composition of the present invention may further comprise an anti-coagulant, a lubricant, a wetting agent, a flavoring agent, an emulsifying agent and an antiseptic agent.

The preparation for parenteral administration may be formulated in the form of injections, creams, lotions, ointments, oils, moisturizers, gels, aerosols and nasal inhalers by methods known in the art. These formulations are described in the literature (Remington's Pharmaceutical Science, 19th ed., Mack Publishing Company, Easton, Pa., 1995), which is a prescription manual commonly known in all pharmaceutical chemistries.

The total effective amount of the composition of the present invention may be administered to a patient in a single dose and may be administered by a fractionated treatment protocol administered over a prolonged period of time in multiple doses. The pharmaceutical composition of the present invention may vary in the content of the active ingredient depending on the degree of the disease. Preferably, the preferred total dose of the pharmaceutical composition of the present invention may be from about 0.01 µg to about 10,000 mg, and most preferably from 0.1 µg to 500 mg, per kilogram of patient body weight per day. However, the dosage of the pharmaceutical composition may be determined depending on various factors such as the formulation method, administration route, and the number of treatments as well as the patient's age, weight, health condition, sex, severity of disease, diet and excretion rate. With this in mind, one of ordinary skill in the art will be able to determine the appropriate effective dose of the composition of the present invention. The pharmaceutical composition according to the present invention is not particularly limited to the formulation, administration route and administration method as long as the effect of the present invention is exhibited.

The present invention provides a food composition for preventing and improving colitis comprising *Lactobacillus sakei* K040706 as an active ingredient.

The food composition using *Lactobacillus sakei* K040706 according to the present invention includes all forms such as functional food, nutritional supplement, health food, and food additives. These types can be prepared in various forms according to conventional methods known in the art.

For example, as a health food, the food composition itself of the present invention can be prepared in the form of tea, juice, and drink and then consumed the form of drinking, granulated, encapsulated and powdered. In addition, the food composition of the present invention can be prepared in the form of a composition by mixing together with a known substance or active ingredient known to have an effect of anti-inflammation.

Functional foods also can be prepared by adding the food composition of the present invention to beverages (including alcoholic beverages), fruits and their processed foods (such as canned fruits, bottled, jam, marmalade, etc.), fish, meats and processed foods (such as ham, sausage, corn beef etc.), breads and noodles (such as udon, buckwheat noodles, ramen, spaghetti, macaroni, etc.), fruit juice, various drinks, cookies, taffy, dairy products (such as butter and cheeses), edible plant oils, margarine, vegetable proteins, retort foods, frozen foods, various seasonings (such as soybean paste, soy sauce, sauce, etc.).

The preferred content of the food composition according to the present invention is not limited thereto, but is preferably 0.01 to 50% by weight in the total weight of the final food product. In order to use the food composition of the present invention in the form of a food additive, it may be used in the form of powder or concentrate.

Some embodiments according to the present invention provide a method for treating a colitis disease in a subject in need thereof, the method comprising administering a composition comprising *Lactobacillus sakei* K040706 (Accession No: KCCM11472P) as an active ingredient to the subject in an amount effective in treating the colitis disease.

Preferably, the colitis disease is selected from the group consisting of acute enteritis, bacterial colitis, bacterial dysentery, cholera, typhoid, traveler's diarrhea, viral colitis, pseudomembranous colitis, amoebic colitis, inflammatory bowel disease, Crohn's disease, ulcerative colitis, ischemic colitis, Behcet's colitis, drug-induced colitis, microscopic colitis, collagenous colitis, lymphocytic colitis and radiation colitis.

As used herein, the term "treatment" or "treating" refers to inhibition of disease development, inhibition of recurrence, alleviation of symptoms, reduction of direct or indirect pathological consequences of disease, a reduction in the rate of disease progression, an improvement in the disease state, an improvement, or alleviation.

The term "effective amount" of the present invention refers to an amount that, when administered to a subject, leads to the improvement, alleviation, treatment, or prevention of the colitis disease. The term "subject" may be an animal, preferably a mammal including humans, animal-derived cells, tissues, or organs. Preferably, the subject may be a patient needed for treatment.

Another embodiments provide the above mentioned method wherein the composition comprises a dead cell or culture preparation of *Lactobacillus sakei* K040706.

Another embodiments provide the above mentioned method wherein the composition is a pharmaceutical composition or a food composition.

In the example of the present invention, heat-inactivated *Lactobacillus sakei* K040706 was administered to mice and DSS (Dextran Sulfate Sodium Salt) was also administered to induce colitis. Then the length was measured by removing the intestines, and the weight of the spleen was measured. As a result of measuring, the length of the intestine was reduced and the weight of the spleen was decreased in the *Lactobacillus sakei* K040706 treated group (FIG. 1).

In addition, the DAI (disease activity index) was measured in terms of the weight loss, the hardness of the excrement, and the degree of bleeding in the excrement in the mouse model of colitis, and MPO activity was measured. As a result, DAI was decreased and MPO activity was inhibited in the *Lactobacillus sakei* K040706 treated group (Table 1 and FIG. 2).

Figure 3:
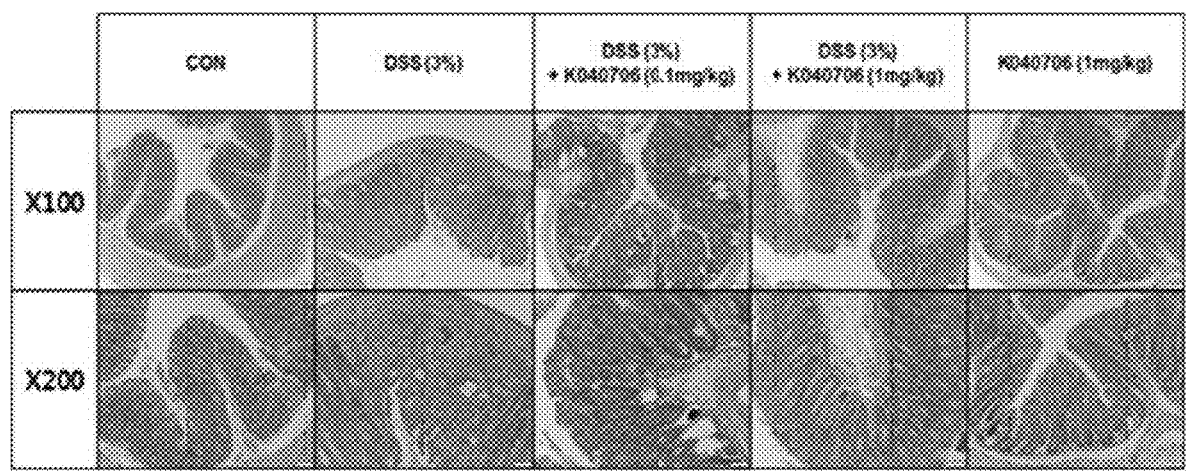
FIG. 3 shows the result of observation through the villus cell damage and restoring the transmission degree of the H & E staining in intestinal tissue of the group treated with *Lactobacillus sakei* K040706 dead cells in a colitis mouse model.

Meanwhile, the intestinal tissues extracted from the mouse model of colitis were observed by H&E staining. As a result, it was confirmed that the damage to the villi and the cell permeability decreased in the *Lactobacillus sakei* K040706 treated group (FIG. 3).

In another example of the present invention, the intestinal tissue extracted from the mouse model of colitis was pulverized and centrifuged, and then the obtained supernatant was subjected to griess test. The amount of iNOS protein expression was measured. As a result, it was found that NO production was decreased and the expression level of iNOS protein was decreased in the *Lactobacillus sakei* K040706 treated group (FIG. 4). In addition, the amounts of IL-6 and IL-1β were measured and it was confirmed that the production of IL-6 and IL-1β was decreased in the *Lactobacillus sakei* K040706 treated group (FIG. 5).

In another example of the present invention, the expression levels of TNF-α, IL-6 and TLR4 mRNA were confirmed by RT-PCR with total RNA extracted from the intestinal tissues of the mouse model of colitis. As a result, it was shown that the expression levels of TNF-α, IL-6, and TLR4 mRNA were decreased in the *Lactobacillus sakei* K040706 treated group (FIG. 6).

On the other hand, the expression levels of NF-κB (p-p65) and STAT3 (p-STAT3) were measured using proteins extracted from the intestinal tissues of a mouse model of colitis. As a result, it was found that the expression level of NF-κB (p-p65) and STAT3 (p-STAT3) were decreased in the *Lactobacillus sakei* K040706 treated group (FIG. 7), confirming that *Lactobacillus sakei* K040706 inhibited the expression of inflammatory cytokines and the phosphorylation of NF-κB and STAT3.

Thus, the present invention provides a pharmaceutical composition and a food composition for preventing or treating colitis comprising *Lactobacillus sakei* K040706 as an active ingredient. Since *Lactobacillus sakei* K040706 of the method of the present invention has an immune enhancement function such as increasing intestinal NO production ability and has a function of reducing intestinal tissue damage, it can be usefully applied to improve and treat colitis.

Hereinafter, the present invention will be described in detail.

However, the following examples are illustrative of the present invention, and the contents of the present invention are not limited to the following examples.

Experimental Method

1. Preparation of Dead Cells

*Lactobacillus sakei* K040706 used in the present invention is a microorganism deposited at Korean Culture Center of Microorganisms (Accession No.: KCCM11472P), which was used in the prior application "Novel *Lactobacillus sakei* K040706 for multifunction and culture method thereof (Korean Patent Application No. 10-2015-0088702)" were used.

*Lactobacillus sakei* K040706 stock (1 ml), stored in a deep freezer at −80° C., was rapidly thawed and cultured on a plate medium. A colony on the plate was inoculated in 5 ml MRS liquid medium and cultured in a thermostat at 30° C. for 24 hours. The cultured cells were centrifuged at 5,000 rpm for 15 minutes at 4° C. to separate the supernatant and the precipitate. The precipitate was washed three times with physiological saline and cells were obtained. The obtained cells were heated at 85° C. for 15 minutes to form dead cells. The resulting dead cells were lyophilized and used for efficacy evaluation.

2. Colitis Mouse Model

ICR male white mice weighing 28 to 30 g were purchased from Orient Bio Co. (Sungnam, KyungKi-Do, Republic of Korea), and were maintained under constant conditions (temperature: 20±2° C., humidity: 40-60%, darkness: 12 hours light/dark cycle), and used for this study.

To induce colitis, the mice were given water containing 3% DSS (Dextran Sulfate Sodium Salt) in drinking water for 15 days. As a control, 5-amino salicylic acid (5-ASA, 50, 100 mg/kg p.o.) was used as an anti-inflammatory agent. Each group was composed of in 6 animals. Seven days prior to induction of colitis in mice, oral administration of the drug and microbial dead cells were carried out, and the experiment was conducted after the last fasting and removal of the DSS. The condition of the mice was examined daily for 5 days during the experiment, and the colitis disease score was calculated based on the criteria in Table 1.

TABLE 1

| Criteria for colitis score | | | |
|---|---|---|---|
| Score | Weight loss (%) | Stool consistency | Occult/gross bleeding |
| 0 | None | Normal | Normal |
| 1 | 1-5 | | |
| 2 | 5-10 | Loose stools | Hemoccult positive |
| 3 | 10-20 | | |
| 4 | >20 | Diarrhea | Gross bleeding |

3. MPO (Myeloperoxidase) Measurement

A portion of the intestine extracted from the colitis-induced mouse model was placed and lysed in lysis buffer (200 mM NaCl, 5 mM EDTA, 10 mM tris, 10% glycerol, 1 mM PMSF, 1 μg/ml leupeptide, 28 μg/ml aprotonine (pH 7.4). The supernatant was obtained by centrifugation at 1,500 g for 15 minutes. The same procedure was repeated 3 times to obtain the supernatant. The obtained supernatant was assayed for MPO production using EIA kits (Hycult biotechnology, Netherlands) according to the manufacturer's instructions.

4. H&E Staining (Hematoxylin and Eosin Staining)

Some of the intestinal tissues extracted from the colitis-induced mouse model were fixed in 4% paraformaldehyde for 24 hours and then washed 3 times with PBS. It was then implanted in an OCT (Optica coherence tomography) compound. The OCT compound block was cut into 8 μm sections, stained with hematoxylin and eosin, and observed with an optical microscope.

In addition, Immunohistochemical staining of 8 μm sections was performed after OCT removal using PBS. $H_2O_2$ was treated for 15 minutes to remove the endogenous peroxidase and reacted with 10% normal goat serum (NGS) for 1 hour. Then, the primary antibody was reacted in a humidity chamber at 4° C. for 12 hours, rinsed thoroughly, and the secondary antibody (biotinylated-goat anti-rabbit IgG, 1:1000, vector, USA) was reacted at room temperature for 1.5 hours and rinsed thoroughly. It was then reacted with avidin for 1 hour. After color development with DAB (diaminobenzidine), it was stained with hematoxylin and observed with an optical microscope.

5. Measurement of NO Production

Nitric oxide production in the culture was evaluated by measuring nitrite (NO2−), an oxide of nitrogen oxide (NO). An intestine tissue of the extract from the colitis-induced mouse model was placed and lysed in lysis buffer (200 mM NaCl, 5 mM EDTA, 10 mM tris, 10% glycerol, 1 mM PMSF, 1 μg/ml leupeptide, 28 μg/ml aprotonine (pH 7.4). The supernatant was obtained by centrifugation at 1,500 g for 15 minutes. The same procedure was repeated 3 times to obtain the supernatant. 100 μL of the obtained supernatant was dispensed into a 96-well plate, and 100 μL of the griess reagent (1% (w/v) sulfanilamide in 5% (v/v) phosphoric acid and 0.1% (w/v) naphtylethylenediamine-HCl) were mixed and incubated in a shaker for 10 min. The absorbance was measured at 540 nm using a microplate reader.

6. Analysis of Immune Index in Tissues

The mid-colon extracted from the colitis mouse model was washed in DMEM medium containing 2% FBS, penicillin, and streptomycin sulfate. The 0.5-cm-sized pieces of the mid-colon were placed into a 24-well plate with 1 ml DMEM medium containing 0.2% FBS and incubated at 37° C. in 5% $CO_2$ for 24 hours. The cells were then harvested and centrifuged to obtain a culture supernatant by removing cells. TNF-α, IL-1β, IL-6 and IL-4 cytokines were analyzed using EIA kit (R&D system, USA) according to the manufacturer's instructions.

7. RT-PCR

Total RNA was extracted from the colonic tissue cells isolated from the colitis mouse model using Easy Blue kits (IntronBiotechnology) according to the manufacturer's instructions. 1 μg of RNA was reverse transcribed using MuLV reverse transcriptase, 1 mM dNTP and oligo dT (0.5 μg/μl) in each sample to synthesize cDNA. The synthesized cDNA was mixed with 1 unit of Tag DNA polymerase, 0.2 mM dNTP, ×10 reaction buffer and 100 pmol of primer to make a total volume of 25 μl. Mixed samples were subjected to PCR using a thermal cycler (Perkin Elmer Cetus, USA).

TABLE 2

|  |  | Base sequence | SEQ ID NO: |
|---|---|---|---|
| iNOS | Sense | 5'-AATGGCAACATCAGGTCGGCCATCACT-3' | 1 |
|  | Anti-sense | 5'-GCTGTGTGTCACAGAAGTCTCGAACTC-3' | 2 |
| COX-2 | Sense | 5'-GGAGAGACTATCAAGATAGT-3' | 3 |
|  | Anti-sense | 5'-ATGGTCAGTAGACTTTTACA-3' | 4 |
| β-actin | Sense | 5'-TCATGAAGTGTGACGTTGACATCCGT-3' | 5 |
|  | Anti-sense | 5'-CCTAGAAGCATTTGCGGTGCACGATG-3' | 6 |

Primer base sequence

8. Western Blot

Proteins were extracted with PRO-PREP (Intron Biotechnology) from the intestinal tissues collected from the colitis mouse model and centrifuged to obtain supernatant. Protein concentration was quantified in the supernatant using Bradford reagent. Proteins were electrophoresed on 10% SDS gel, and proteins in the gel were transferred to PVDF membrane. It was then blocked with 5% skim milk for 1 hour. Then, the membrane was treated with anti-iNOS, anti-p65, anti-pIκB, anti-IκB and anti-COX2 as primary antibodies and reacted overnight, respectively. Subsequently, the membrane was washed three times at 10-minute intervals using TBST, and then reacted with anti-rabbit and anti-mouse as secondary antibodies, respectively, for 2 hours at room temperature. After washing three times with TBST at intervals of 10 minutes, ECL color development was performed. The expression level was observed using chemiluminescence.

9. Statistical Analysis

The values of the test values were expressed as mean±SD, and the analysis was significant with Student's t-test.

Example 1

Anti-Colitis Effect of L. sakei K040706 in a Colitis Mouse Model

A mouse model of colitis induced by DSS (Dextran Sulfate Sodium Salt), a substance that artificially damages the wall of the intestine and causes acute colitis, was used to determine if L. sakei K040706 is effective on colitis. As described in the above experimental method, 3% DSS was administered in a water bottle for 12 days to induce acute colitis, and anti-inflammatory effect was confirmed by administering L. sakei K040706 at the same time. The length of the colon was measured by sacrificing the colitis mouse model and the spleen was excised and weighed. In addition, as shown in Table 1, the DAI (disease activity index) was measured in terms of the weight reduction, the hardness of the excrement, and the degree of hemorrhage in the excreta, and the effect of L. sakei K040706 on MPO activity was measured.

For morphological observation of intestinal tissues in a colitis mouse model, intestinal tissues were extracted from mice and fixed in a 4% formaldehyde solution for 24 hours, and then sufficiently washed with flowing water. Thereafter, dehydration was performed stepwise using 78%, 80%, 90%, and 100% ethanol, followed by paraffin permeation and embedding. The embedded tissues were stained with H&E (hematoxin and eosin) after being sliced at a thickness of about 8 μm with a thin section slice, and the changes of intestinal tissues were observed under an optical microscope.

Figure 1B:
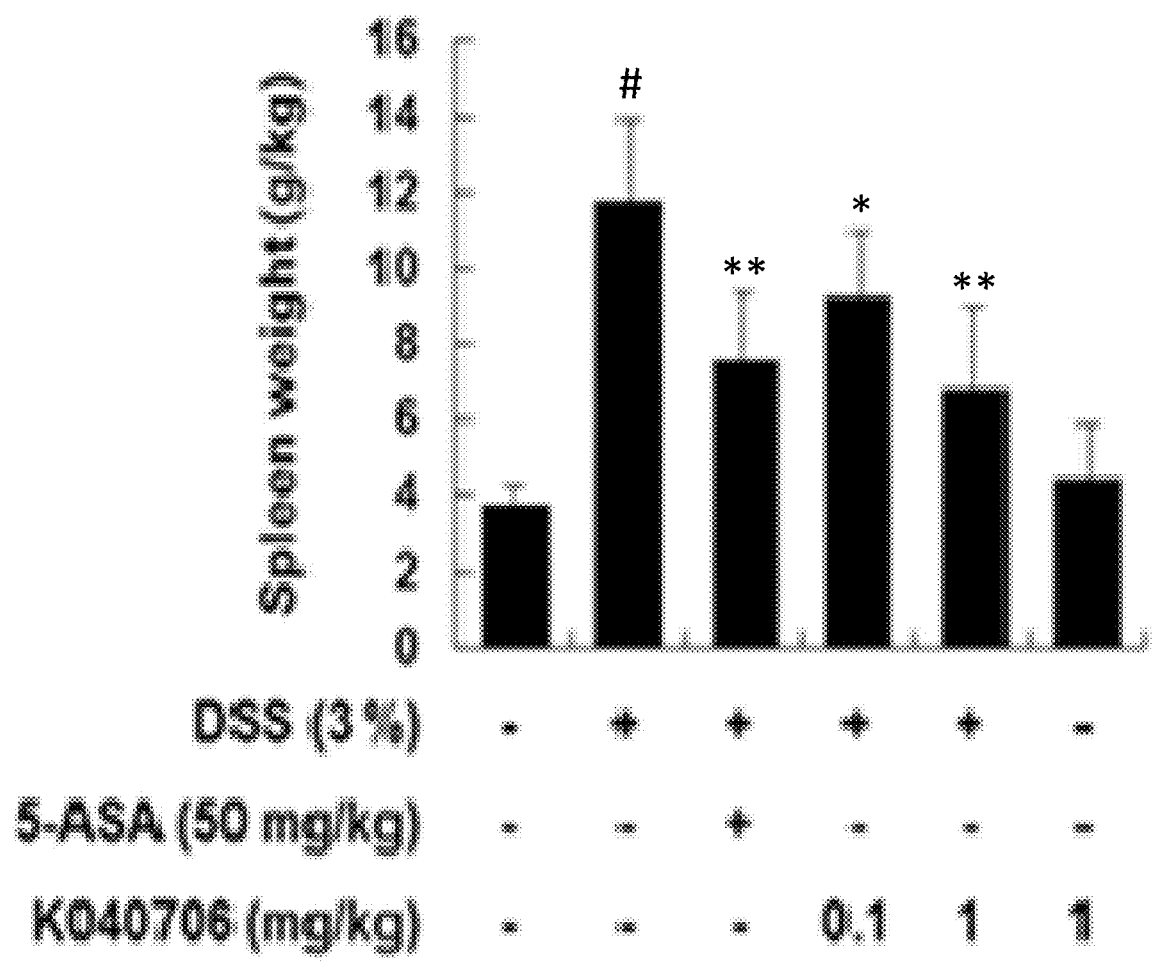

As a result, as shown in FIG. 1, the intestinal length of DSS induced colitis group was decreased, whereas the intestinal length of L. sakei K040706 treated group was increased (FIG. 1A). In addition, the weight of the spleen was increased in the colitis mouse model, whereas the weight of spleen was decreased in the group administered with L. sakei K040706 (FIG. 1B).

Figure 2A:
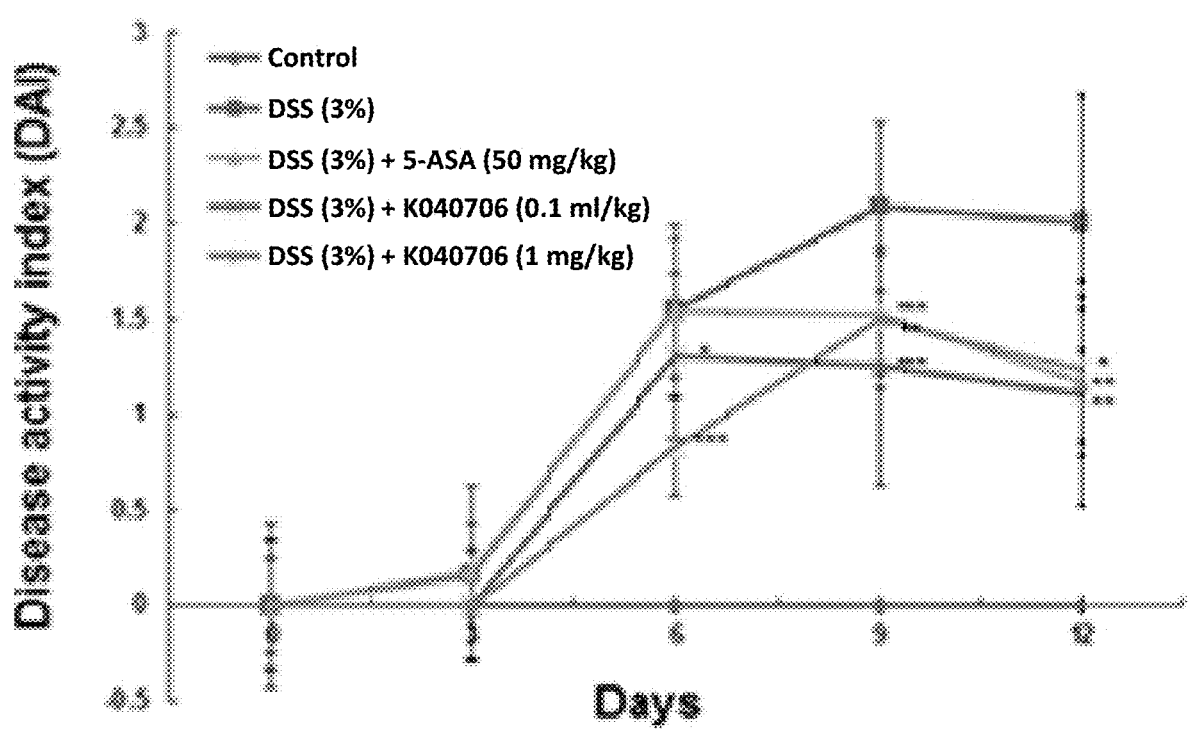
FIGS. 2A-B show the results of measuring the change in the disease activity index (DAI) and the myeloperoxidase (MPO) activity of the intestinal tissue. *Lactobacillus sakei* K040706 dead cells were administered to colitis mouse model and observed for 12 days (Means±SD; *p<0.05, p<0.01, *p<0.001 vs. DSS (colitis inducing drug) alone group).
Figure 2B:
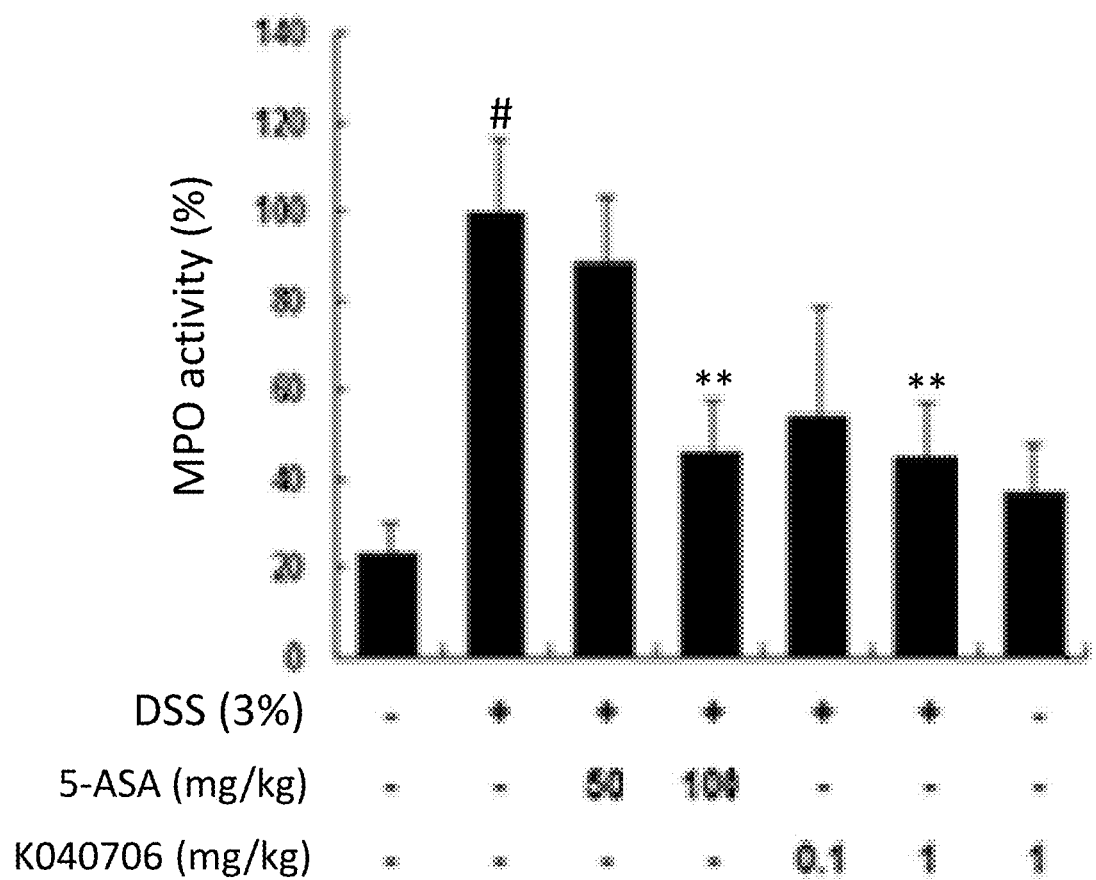

On the other hand, as shown in FIG. 2, DAI was increased in DSS colitis induced group, but DAI was decreased in L. sakei K040706 treated group (FIG. 2A). MPO activity was increased in the colitis mouse model, but MPO activity was inhibited when L. sakei K040706 was administered (FIG. 2B).

In addition, as shown in FIG. 3, villus damage and cell permeability were increased in the DSS induced colitis group, but villus damage and cell permeation were decreased in the L. sakei K040706 treated group.

Thus, it was confirmed that L. sakei K040706 inhibits intestinal tissue damage and inhibits colitis.

Example 2

Effect of L. sakei K040706 on iNOS Expression in a Colitis Mouse Model

To investigate the effect of L. sakei K040706 on iNOS expression in DSS-induced colitis mouse models, the following experiment was conducted.

The intestinal tissues were collected from the colitis mouse model, pulverized and centrifuged to obtain a supernatant as in the above-described experimental method. The supernatant was mixed at a ratio of 1:1 with the griess reagent, placed in a 96-well plate, and reacted on a shaker for 10 minutes. Then absorbance was measured at 540 nm using a microplate reader. And also the amount of iNOS protein expression was measured by Western blotting using the extracted supernatant.

Figure 4A:
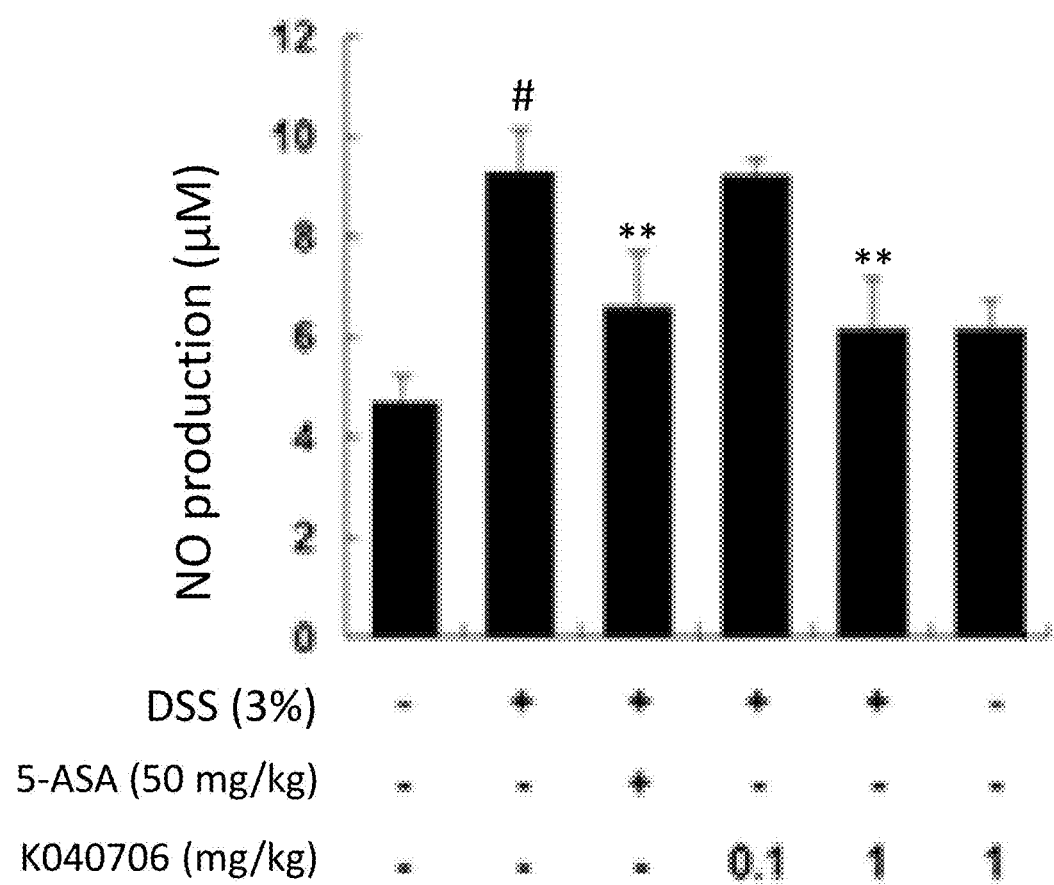
FIGS. 4A-B show that the amount of NO production and the amount of iNOS protein expression were measured in the intestinal tissue of a colitis mouse model administered with *Lactobacillus sakei* K040706 dead cells.
Figure 4B:
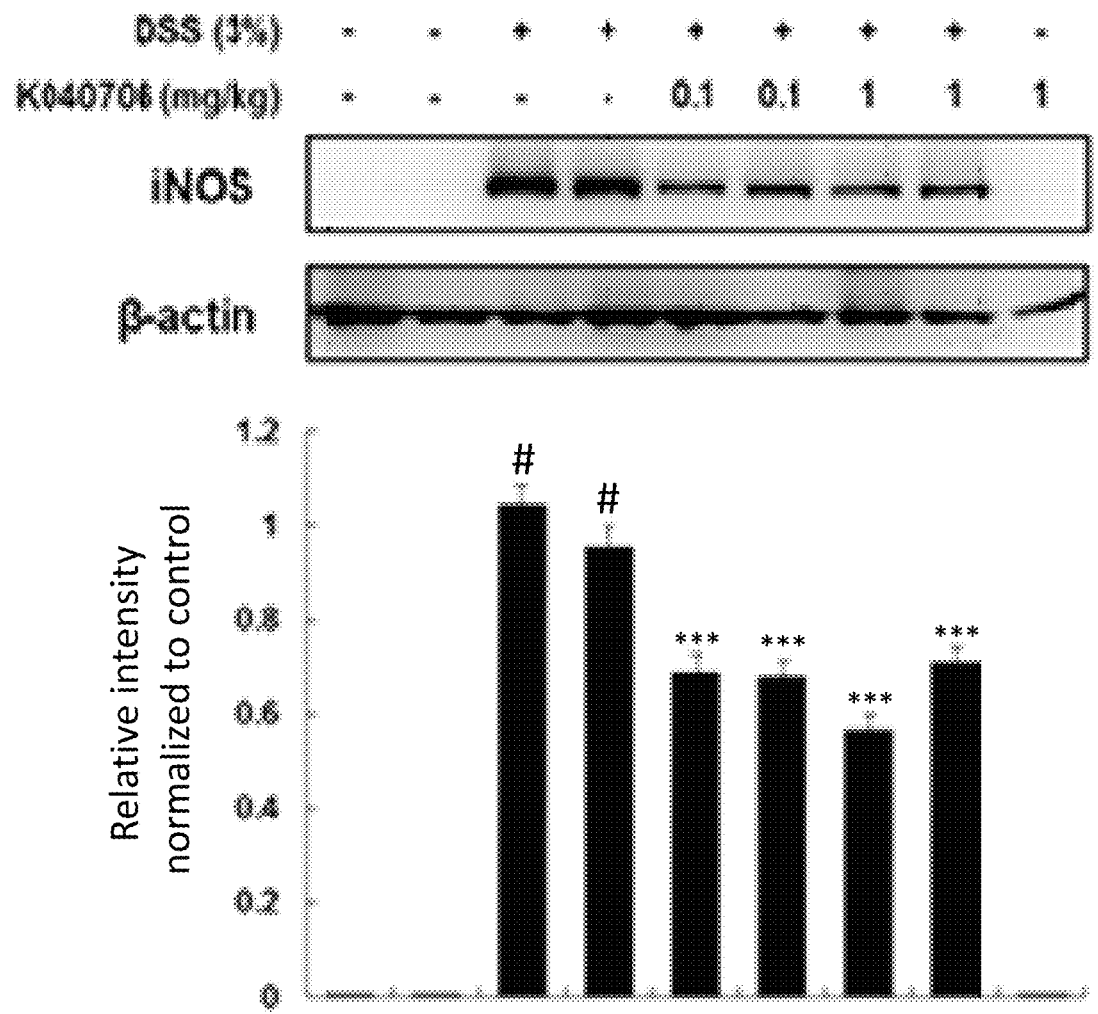
Figure 5A:
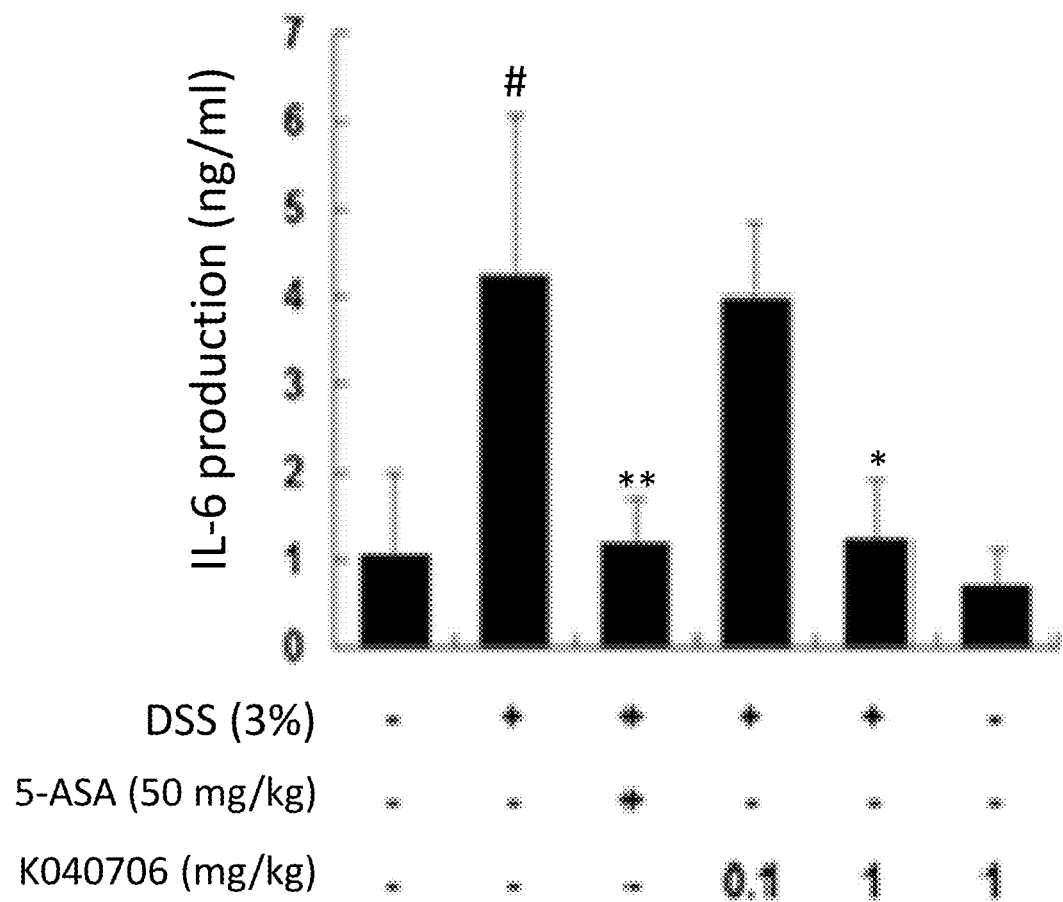
FIGS. 5A-B show the concentration of inflammatory cytokines of IL-6 (A) and IL-1β (B) in a colitis mouse model administered with *Lactobacillus sakei* K040706 dead cells (*p<0.05, p<0.01, *p<0.001 vs. DSS (colitis inducing drug) alone group).
Figure 5B:
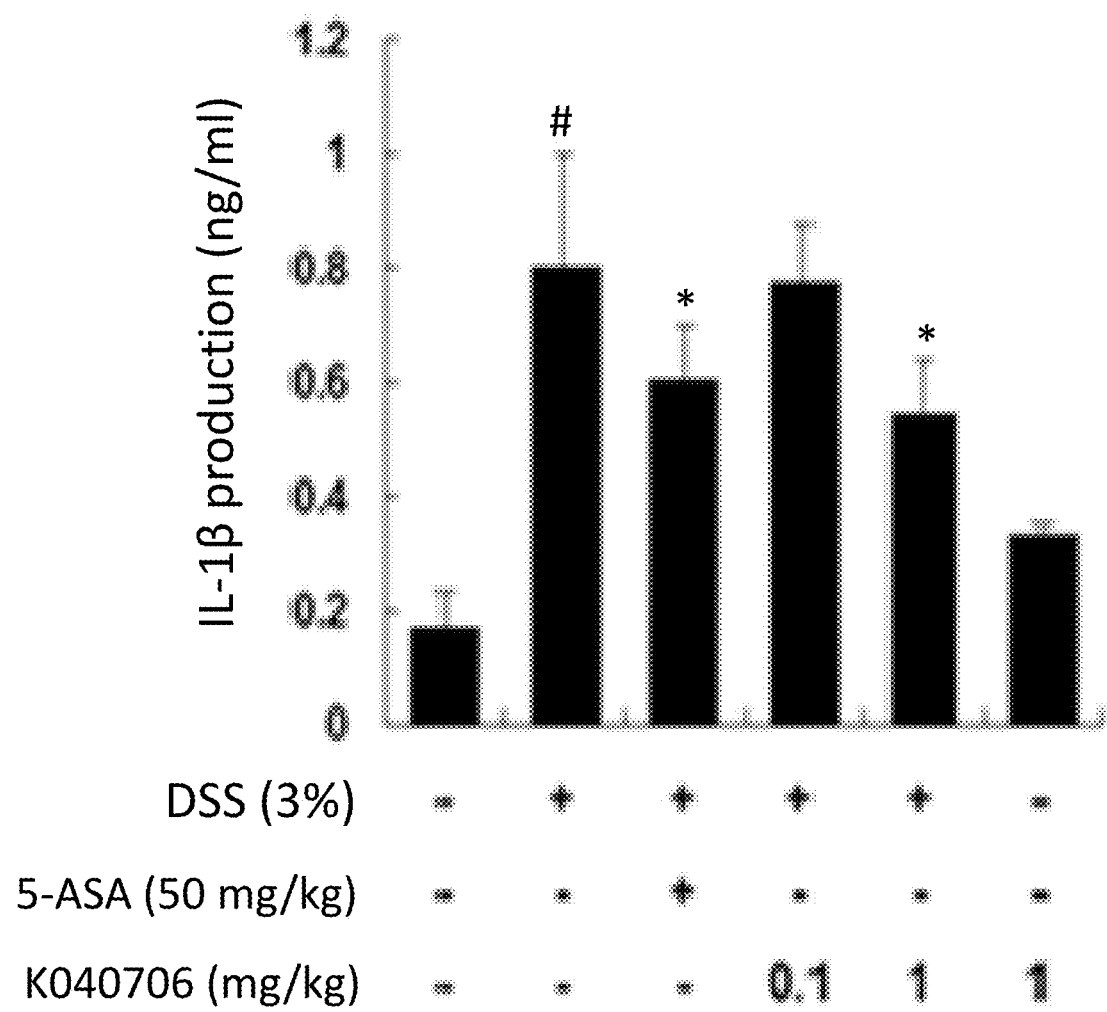

As a result, as shown in FIG. 4, NO production was increased in the DSS-induced colitis mouse group, whereas NO production was decreased in the group administered with *L. sakei* K040706 (FIG. 4A). In addition, the expression level of iNOS protein was increased in the DSS-induced colitis mouse group, but the expression level of iNOS protein was decreased in the group administered with *L. sakei* K040706 (FIG. 4B).

It was confirmed that *L. sakei* K040706 inhibit the intestinal NO production by inhibiting expression of iNOS protein.

Example 3

Effect of *L. sakei* K040706 on Inflammatory Factor Production in Colitis Mouse Model To investigate the effect of *L. sakei* K040706 on production of inflammatory factors in DSS-induced colitis mouse models, the following experiment was conducted.

The intestinal tissues were collected from the DSS-induced colitis mouse model, placed in a cell culture medium, pulverized, and centrifuged to obtain a supernatant as in the above-described experimental method. Then, the amount of IL-6 and IL-1β in the extracted supernatant was measured.

As a result, as shown in FIG. 5, IL-6 and IL-1β production was increased in the DSS-induced colitis mouse group, but IL-6 and IL-1β production were decreased in the group administered with *L. sakei* K040706.

Thus, it was confirmed that *L. sakei* K040706 inhibits the production of IL-6 and IL-1β, which are inflammatory factors, resulting in possessing an anti-colitis effect.

Example 4

Effect of *L. sakei* K040706 on Inflammatory Cytokine mRNA Expression in Colitis Mouse Model To investigate the effect of *L. sakei* K040706 on inflammatory cytokine mRNA expression in DSS-induced colitis mouse models, the following experiment was conducted.

The intestinal tissues were collected from the colitis mouse model, pulverized and centrifuged to extract total RNA from the precipitate as in the above-described experimental method. RT-PCR was performed to synthesize cDNA from the extracted RNA and the amount of mRNA expression of TNF-α, IL-6 and TLR4 was confirmed.

Figure 6A:
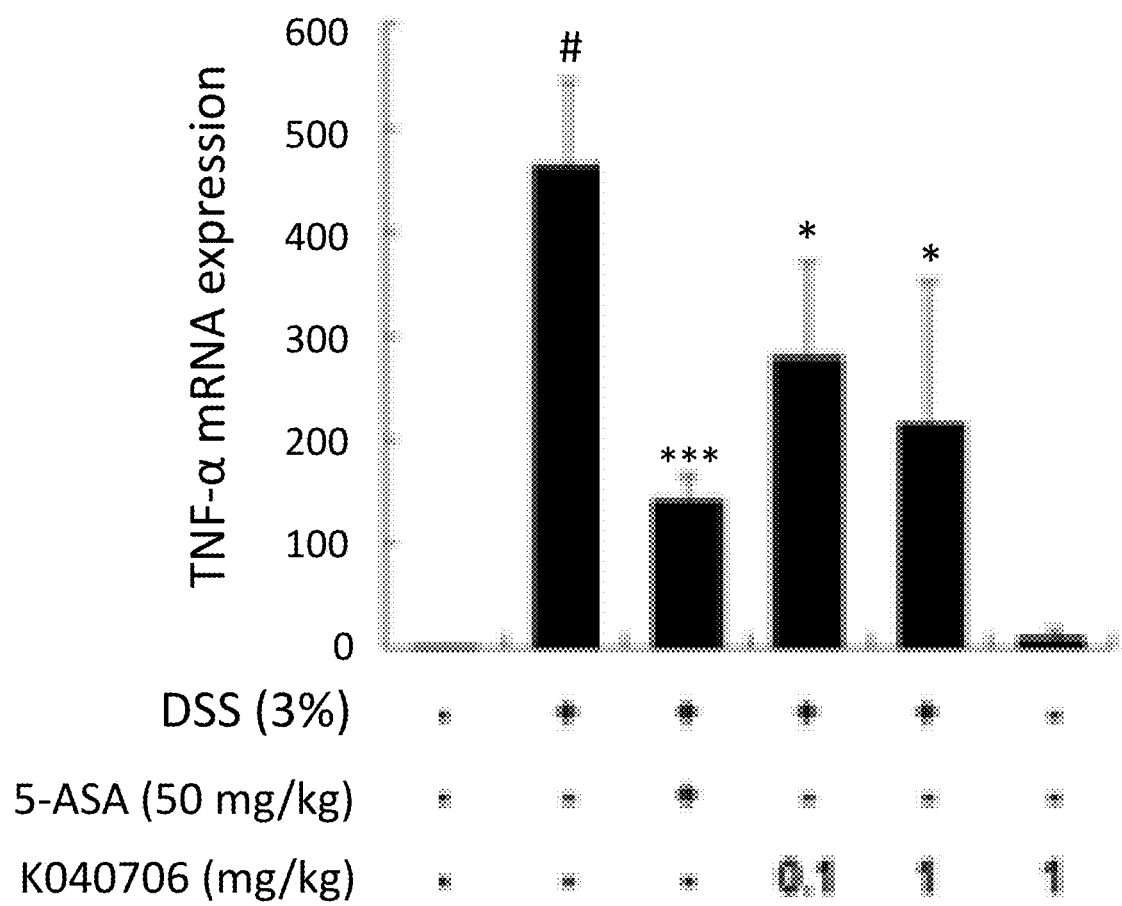
FIGS. 6A-C show the mRNA expression level of pro-inflammatory modulators of TNF-α, IL-6 and TLR4 in a colitis mouse model administered with *Lactobacillus sakei* K040706 dead cells (*p<0.05, p<0.01, *p<0.001 vs. DSS (colitis inducing drug) alone group).
Figure 6B:
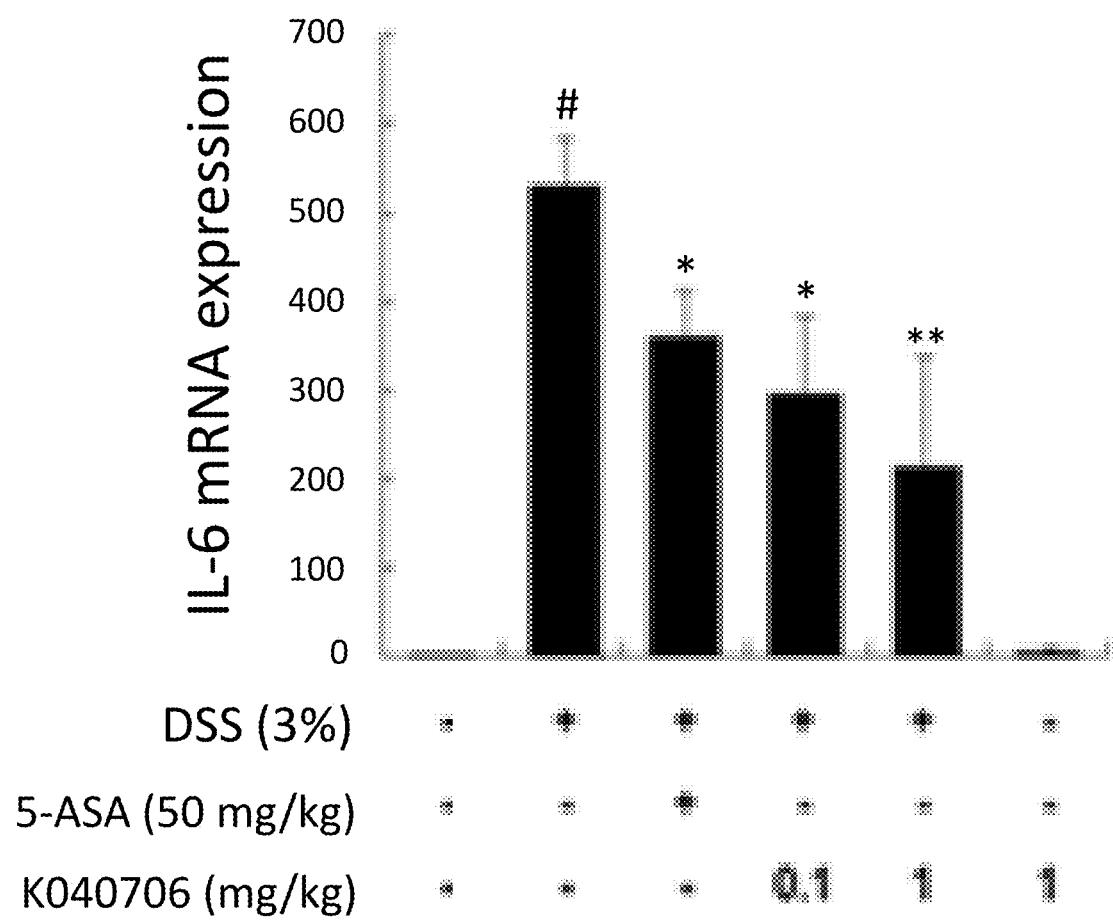
Figure 6C:
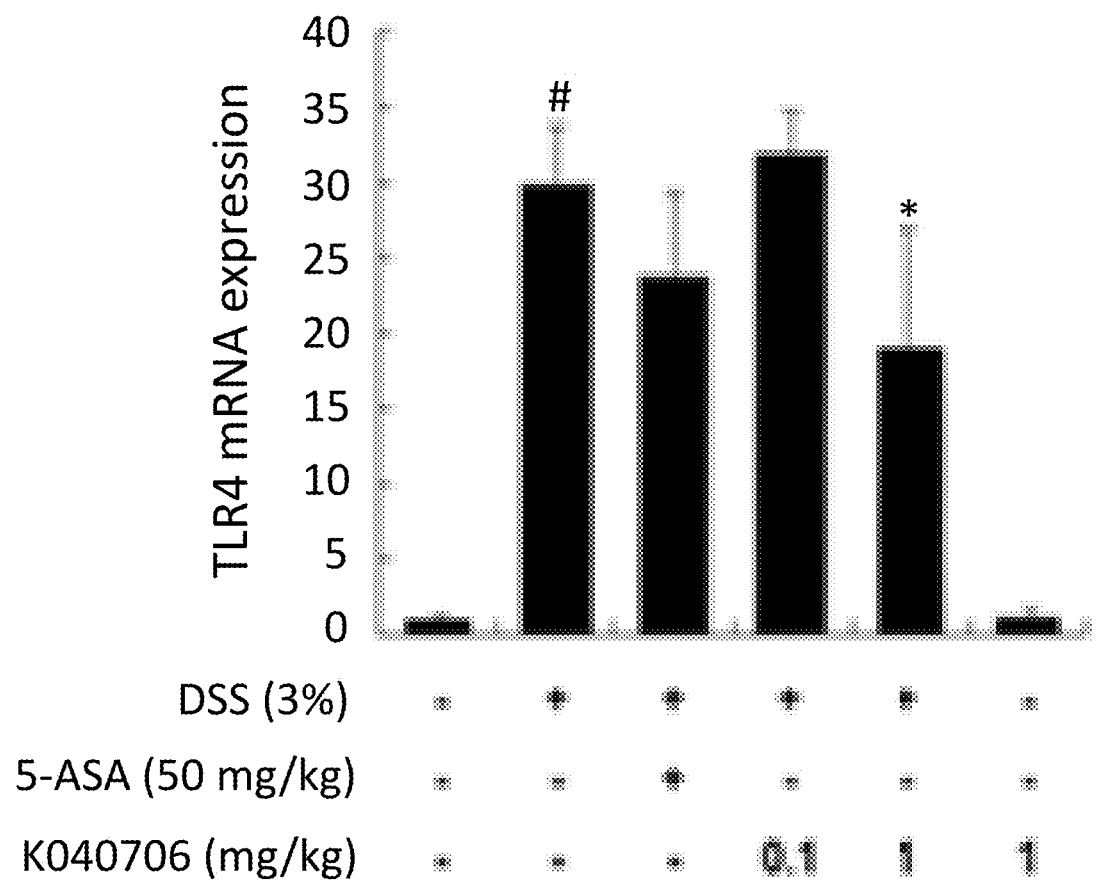

As a result, as shown in FIG. 6, the expression of TNF-α (FIG. 6A) and IL-6 (FIG. 6B) mRNA, which are inflammatory cytokine, in the intestinal tissues of DSS-induced colitis mouse group was increased. But the expression of TNF-α and IL-6 mRNA was decreased in the group administered with *L. sakei* K040706. In addition, the expression of TLR4 (FIG. 6C) mRNA was increased in DSS-induced mouse colitis group, but the expression level of TLR4 mRNA was decreased in the group administered with *L. sakei* K040706.

Thus, it was confirmed that *L. sakei* K040706 inhibited the expression of inflammatory cytokines and decreased the expression of endotoxin receptors, thereby inhibiting the intracellular inflammatory responses caused by harmful bacteria.

Example 5

Effect of *L. sakei* K040706 on NF-κB and STAT 3 Activation in Colitis Mouse Model To investigate the effect of *L. sakei* K040706 on the activation of NF-κB and STAT3 (Signal transducer and activator of transcription 3), the major transcription factors controlling the expression of various inflammatory markers, the following experiment was conducted.

Proteins were extracted from the intestinal tissues collected from the colitis mouse model according to the above-described experimental method, and the concentrations of the proteins were quantified and subjected to SDS-PAGE. Then, the proteins were transferred to PVDF membrane, reacted with primary antibody overnight, and reacted with secondary antibody for 2 hours. ECL expression method was applied to observe the amount of protein expression.

Figure 7:
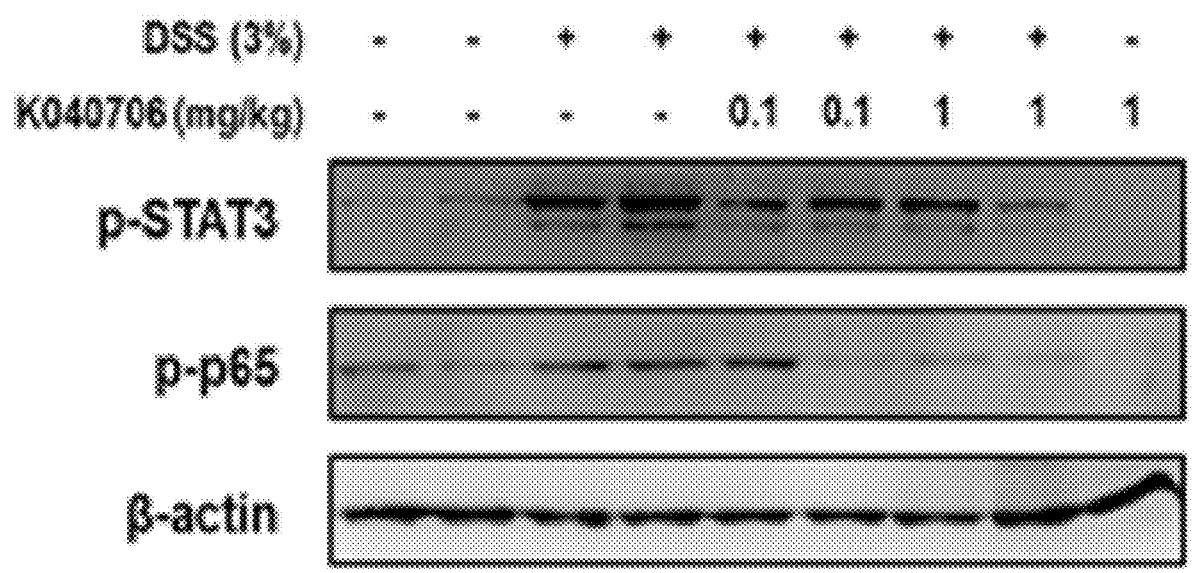
FIG. 7 shows the protein expression level of STAT3 (p-STAT3) and NF-κB (p-p65) inflammatory transcription factors in a colitis mouse model administered with *Lactobacillus sakei* K040706 dead cells.

As a result, as shown in FIG. 7, phosphorylation of NF-κB (p-p65) and STAT3 (p-STAT3) was increased in DSS-induced colitis mouse model group. Phosphorylation of NF-κB (p-p65) and STAT3 (p-STAT3) was decreased in the group administered with *L. sakei* K040706.

Thus, it was confirmed that *L. sakei* K040706 inhibited the phosphorylation of NF-κB and STAT3 and their activation, thereby reducing the expression of inflammation-related indicators.

As described above, the present invention provides a pharmaceutical composition and food composition for preventing and treating colitis, comprising *Lactobacillus sakei* K040706 as an active ingredient. Since *Lactobacillus sakei* K040706 of the present invention is capable of enhancing immune function such as increasing intestinal NO production ability and reducing the damage of intestinal tissue, *Lactobacillus sakei* K040706 may be useful for improving and treating colitis.

What is claimed is:

1. A method for treating a colitis disease in a subject in need thereof, the method comprising administering a composition consisting essentially of *Lactobacillus sakei* K040706 (Accession No: KCCM11472P) as an active ingredient to the subject in an amount effective in treating the colitis disease,
    wherein the colitis disease is selected from the group consisting of acute enteritis, bacterial colitis, bacterial dysentery, cholera, typhoid, traveler's diarrhea, viral colitis, pseudomembranous colitis, amoebic colitis, inflammatory bowel disease, Crohn's disease, ulcerative colitis, ischemic colitis, Behcet's colitis, drug-induced colitis, microscopic colitis, collagenous colitis, lymphocytic colitis and radiation colitis.

2. The method of claim 1, wherein the composition consists essentially of a dead cell or culture preparation of *Lactobacillus sakei* K040706.

3. The method of claim 1, wherein the composition is a pharmaceutical composition or a food composition.

* * * * *

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: iNOS sense

<400> SEQUENCE: 1

-continued

```
aatggcaaca tcaggtcggc catcact                                          27

<210> SEQ ID NO 2
<211> LENGTH: 27
<212> TYPE: DNA
<213> ORGANISM: Artificial Sequence
<220> FEATURE:
<223> OTHER INFORMATION: iNOS anti-sense

<400> SEQUENCE: 2
gctgtgtgtc acagaagtct cgaactc                                          27

<210> SEQ ID NO 3
<211> LENGTH: 20
<212> TYPE: DNA
<213> ORGANISM: Artificial Sequence
<220> FEATURE:
<223> OTHER INFORMATION: COX-2 sense

<400> SEQUENCE: 3
ggagagacta tcaagatagt                                                  20

<210> SEQ ID NO 4
<211> LENGTH: 20
<212> TYPE: DNA
<213> ORGANISM: Artificial Sequence
<220> FEATURE:
<223> OTHER INFORMATION: COX-2 anti-sense

<400> SEQUENCE: 4
atggtcagta gacttttaca                                                  20

<210> SEQ ID NO 5
<211> LENGTH: 26
<212> TYPE: DNA
<213> ORGANISM: Artificial Sequence
<220> FEATURE:
<223> OTHER INFORMATION: beta actin sense

<400> SEQUENCE: 5
tcatgaagtg tgacgttgac atccgt                                           26

<210> SEQ ID NO 6
<211> LENGTH: 26
<212> TYPE: DNA
<213> ORGANISM: Artificial Sequence
<220> FEATURE:
<223> OTHER INFORMATION: beta actin anti-sense

<400> SEQUENCE: 6
cctagaagca tttgcggtgc acgatg                                           26
```